United States Patent
Shigeta et al.

(10) Patent No.: US 11,175,158 B2
(45) Date of Patent: Nov. 16, 2021

(54) PEDOMETER DEVICE, STEP COUNTING METHOD, AND RECORDING MEDIUM

(71) Applicant: ASAHI KASEI KABUSHIKI KAISHA, Tokyo (JP)

(72) Inventors: Keisuke Shigeta, Tokyo (JP); Shiro Kobayashi, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 182 days.

(21) Appl. No.: 16/296,210

(22) Filed: Mar. 7, 2019

(65) Prior Publication Data

US 2019/0204112 A1 Jul. 4, 2019

Related U.S. Application Data

(63) Continuation of application No. PCT/JP2017/032088, filed on Sep. 6, 2017.

(30) Foreign Application Priority Data

Sep. 9, 2016 (JP) .............................. JP2016-176606

(51) Int. Cl.
*G01C 22/02* (2006.01)
*G01C 22/00* (2006.01)
(Continued)

(52) U.S. Cl.
CPC .............. *G01C 22/006* (2013.01); *A61B 5/11* (2013.01); *A61B 5/112* (2013.01); *A61B 5/7203* (2013.01);
(Continued)

(58) Field of Classification Search
CPC .................................................. G01C 22/006
See application file for complete search history.

(56) References Cited

U.S. PATENT DOCUMENTS 4,962,469 A * 10/1990 Ono ..................... G01C 22/006
235/105
5,065,414 A * 11/1991 Endou .................. G01C 22/006
377/24.2
(Continued)

FOREIGN PATENT DOCUMENTS

| JP | 2005114537 A | 4/2005 |
| JP | 2012008637 A | 1/2012 |
| JP | 2012145457 A | 8/2012 |

OTHER PUBLICATIONS

International Search Report for International Patent Application No. PCT/JP2017/032088, issued by the Japan Patent Office dated Oct. 31, 2017.
(Continued)

*Primary Examiner* — Alvin A Hunter

(57) ABSTRACT

To reduce false counts of a device that counts a user's step count. A pedometer device, a step counting method, and a recording medium are provided. The pedometer devices includes: an acquiring unit that acquires a sensor signal output by a sensor carried by a user; an extracting unit that extracts a feature quantity from the sensor signal; a storage unit that stores a walking model which represents walking motions, the walking model being formed based on a feature quantity extracted from a sensor signal corresponding to a predetermined number of steps of walking; a comparing unit that compares the feature quantity extracted at the extracting unit with the walking model; and a deciding unit that decides whether the user has walked a predetermined number of steps, based on a result of the comparison performed by the comparing unit.

6 Claims, 9 Drawing Sheets

(51) Int. Cl.
*A61B 5/00* (2006.01)
*G06M 3/12* (2006.01)
*A61B 5/11* (2006.01)
*G06M 3/00* (2006.01)
*A63B 24/00* (2006.01)

(52) U.S. Cl.
CPC .......... *A61B 5/7221* (2013.01); *A61B 5/7246* (2013.01); *A61B 5/7267* (2013.01); *A63B 24/0062* (2013.01); *G06M 3/00* (2013.01); *G06M 3/12* (2013.01); *A63B 2220/34* (2013.01); *A63B 2220/40* (2013.01)

(56) References Cited

U.S. PATENT DOCUMENTS

| | | | | |
|---|---|---|---|---|
| 6,334,848 | B1 * | 1/2002 | Wong | A61B 5/02438 600/481 |
| 6,349,126 | B2 * | 2/2002 | Ogawa | G01C 22/006 377/24.2 |
| 6,823,036 | B1 * | 11/2004 | Chen | G01C 22/006 377/24.2 |
| 7,827,000 | B2 * | 11/2010 | Stirling | A61B 5/1118 702/141 |
| 7,962,309 | B2 * | 6/2011 | Meriheina | G01C 21/10 702/141 |
| 8,734,296 | B1 * | 5/2014 | Brumback | A61B 5/1118 482/8 |
| 2002/0107649 | A1 | 8/2002 | Takiguchi | |
| 2006/0158173 | A1 | 7/2006 | Takiguchi | |
| 2006/0161079 | A1 | 7/2006 | Choi | |
| 2011/0177848 | A1 | 7/2011 | Tanabe | |
| 2011/0231152 | A1 | 9/2011 | Kawabe | |
| 2016/0001131 | A1 | 1/2016 | Radecka | |
| 2018/0192917 | A1 | 7/2018 | Piijl | |

OTHER PUBLICATIONS

International Preliminary Report on Patentability for International Application No. PCT/JP2017/032088, issued by the International Bureau of WIPO dated Mar. 12, 2019.

Office Action issued for counterpart Japanese Application No. 2018-538437, issued by the Japanese Patent Office dated Nov. 12, 2019 (drafted on Oct. 31, 2019).

Zihao Tang et al., Self-adaptive Step Counting on Smartphones under Unrestricted Stepping Modes, 2016 IEEE 40th Annual Computer Software and Applications Conference (COMPSAC), Aug. 25, 2016, p. 788-p. 797.

* cited by examiner

ADVANCING DIRECTION CANDIDATES

| ADVANCING DIRECTION CANDIDATES | SIMILARITY WITH WALKING MODEL | SIMILARITY WITH NON-WALKING MODEL |
|---|---|---|
| a | $S_{a1}$ | $S_{a2}$ |
| b | $S_{b1}$ | $S_{b2}$ |
| c | $S_{c1}$ | $S_{c2}$ |
| ... | ... | ... |
| I | $S_{I1}$ | $S_{I2}$ |

FIG. 7

PEDOMETER DEVICE, STEP COUNTING METHOD, AND RECORDING MEDIUM

The contents of the following Japanese patent application(s) are incorporated herein by reference:
NO. 2016-176606 filed in JP on Sep. 9, 2016, and
NO. PCT/JP2017/032088 filed on Sep. 6, 2017.

BACKGROUND

1. Technical Field

The present invention relates to a pedometer device, a step counting method, and a recording medium.

2. Related Art

Conventional devices that detect walking motions of users each include an angular velocity sensor, and an acceleration sensor, and decide whether or not a motion of a user is a walking motion according to the inclination of acceleration in an advancing direction at the time point when the acceleration of the user in the vertical direction shows a local maximum (see Patent Literature 1, for example).

Patent Literature 1: Japanese Patent Application Publication No. 2005-114537

SUMMARY

However, such detection of a walking motion based on the inclination of acceleration inadvertently detects, as a walking motion, even a motion not involving travelling, such as stamp, of a user, thus leading to frequent false detection. Accordingly, if the number of steps that a user walked is counted based on detection of a walking motion, the count result includes significant errors in some cases. In addition, a method of accurately detecting information about user's advancing directions has also been asked for.

(Item 1)
A pedometer device may include an acquiring unit that acquires a sensor signal output by a sensor carried by a user.

The pedometer device may include an extracting unit that extracts a feature quantity from the sensor signal.

The pedometer device may include a storage unit that stores a walking model which represents walking motions, the walking model being formed based on a feature quantity extracted from a sensor signal corresponding to a predetermined number of steps of walking.

The pedometer device may include a comparing unit that compares the feature quantity extracted at the extracting unit with the walking model.

The pedometer device may include a deciding unit that decides whether the user has walked a predetermined number of steps, based on a result of the comparison performed by the comparing unit.

(Item 2)
The storage unit may store a non-walking model which represents non-walking motions, the non-walking model being formed based on a feature quantity extracted from a sensor signal corresponding to a non-walking motion.

The comparing unit may compare the feature quantity extracted at the extracting unit with the non-walking model.

(Item 3)
The pedometer device may include an estimating unit that estimates a time period during which the user apparently has made a walking motion.

(Item 4)
The time period may be an estimated period during which the user apparently has walked a predetermined number of steps.

(Item 5)
The estimating unit may estimate the time period based on a time waveform of the sensor signal.

(Item 6)
The extracting unit may extract a feature quantity of the sensor signal for an at least one candidate of an advancing direction of the user.

The comparing unit may compare, with the walking model, the feature quantity extracted for the at least one candidate of the advancing direction.

The deciding unit may further decide the advancing direction based on a result of the comparison performed by the comparing unit.

(Item 7)
The sensor may include an acceleration sensor.

(Item 8)
The sensor may include an angular velocity sensor.

(Item 9)
A step counting method may include acquiring a sensor signal output by a sensor carried by a user.

The step counting method may include extracting a feature quantity from the sensor signal.

The step counting method may include storing a walking model which represents walking motions, the walking model being formed based on a feature quantity extracted from a sensor signal corresponding to a predetermined number of steps of walking.

The step counting method may include comparing the feature quantity extracted in the extracting with the walking model.

The step counting method may include deciding whether the user has walked a predetermined number of steps, based on a result of the comparison.

(Item 10)
A program for causing a computer to function as the pedometer device according to any one of the items 1 to 8.

The summary clause does not necessarily describe all necessary features of the embodiments of the present invention. The present invention may also be a sub-combination of the features described above.

BRIEF DESCRIPTION OF THE DRAWINGS

FIG. 7 illustrates an exemplary comparison result output by the comparing unit 150 according to the present embodiment.

DESCRIPTION OF EXEMPLARY EMBODIMENTS

Hereinafter, (some) embodiment(s) of the present invention will be described. The embodiment(s) do(es) not limit the invention according to the claims, and all the combinations of the features described in the embodiment(s) are not necessarily essential to means provided by aspects of the invention.

Figure 1:
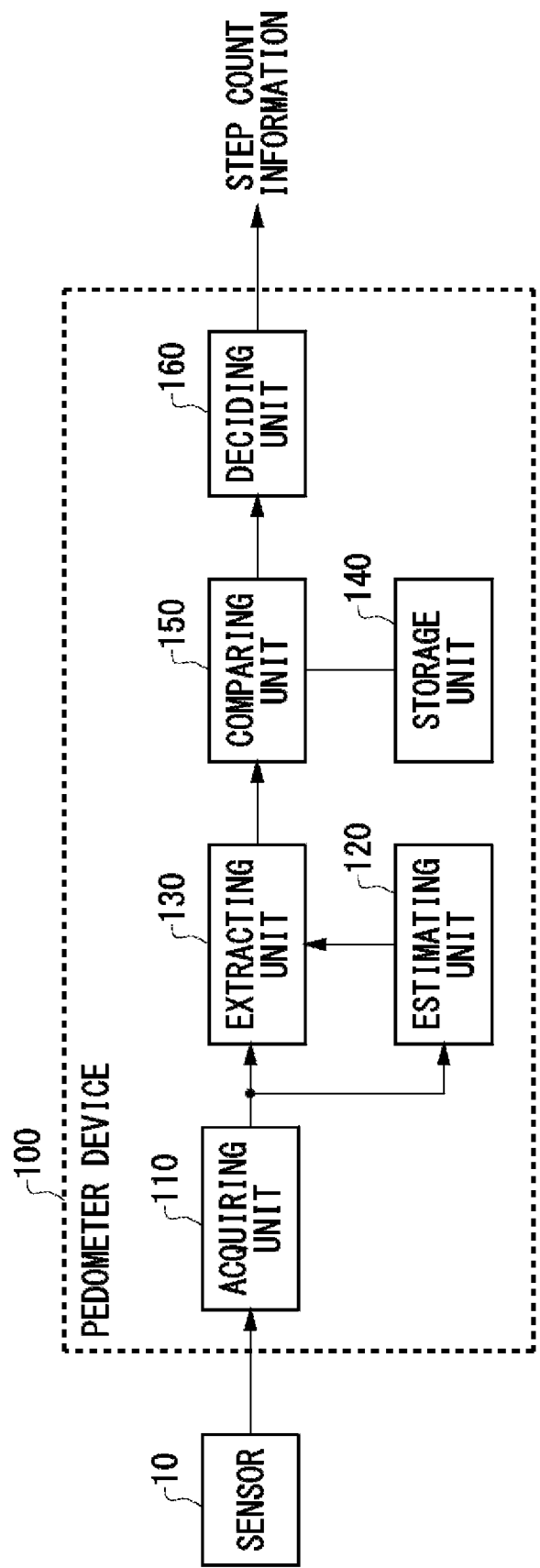
FIG. 1 illustrates an exemplary configuration of a pedometer device 100 according to the present embodiment along with a sensor 10.

FIG. 1 illustrates an exemplary configuration of a pedometer device 100 according to the present embodiment along with a sensor 10. The pedometer device 100 compares a feature quantity of a sensor signal in an estimated time period during which a user apparently has walked a predetermined number of steps with a walking model which represents walking motions to thereby precisely count the number of steps of the user. Note that the walking model is acquired in advance based on feature quantities extracted from sensor signals corresponding to a predetermined number of steps of walking. The pedometer device 100 includes an acquiring unit 110, an estimating unit 120, an extracting unit 130, a storage unit 140, a comparing unit 150, and a deciding unit 160.

Here, the sensor 10 is carried by the user, and outputs a sensor signal corresponding to a motion of the user. The sensor is desirably worn at the waist or the like of the user. The sensor 10 may include multiple types of sensors. The sensor 10 includes an acceleration sensor, for example. In addition, the sensor 10 may include an angular velocity sensor. The sensor 10 is not limited to an acceleration sensor, and an angular velocity sensor as along as it can detect a motion of the user, and may include a speed sensor, a barometer, and/or a geomagnetic sensor, and the like.

The acquiring unit 110 acquires a sensor signal output by the sensor 10 carried by the user. The acquiring unit 110 acquires an output signal from the sensor 10 corresponding to a motion such as a walking motion or a stopping motion of the user. For example, if the user walks, the acquiring unit 110 acquires a sensor signal associated with walking of the user from the sensor 10. Note that the pedometer device 100 and sensor 10 may be housed in one housing, and in this case the acquiring unit 110 may acquire a sensor signal directly from the sensor 10 in the housing. In addition, the housing may be part of a mobile terminal or the like.

In addition, the pedometer device 100 and sensor 10 may be physically separated apart, and in this case the acquiring unit 110 may acquire a sensor signal through wireless communication or the like. In addition, the acquiring unit 110 may acquire a sensor signal that is obtained in advance through detection by the sensor 10, and stored on an external storage or the like. In this case, the acquiring unit 110 may acquire a sensor signal by accessing the external storage or the like through wired communication, wireless communication, network connection or the like. The acquiring unit 110 may supply the acquired sensor signal to the estimating unit 120 and extracting unit 130.

The estimating unit 120 estimates a time period during which the user apparently has made a walking motion. Based on a sensor signal, the estimating unit 120 estimates, as a time period, an estimated period during which the user apparently has walked a predetermined number of steps. The estimating unit 120 may estimate the period based on the time waveform of the sensor signal. The estimating unit 120 may supply the estimated period to the extracting unit 130.

The extracting unit 130 extracts a feature quantity from a sensor signal. The extracting unit 130 may extract a feature quantity of a sensor signal for each estimated period. The extracting unit 130 extracts a feature quantity including the amplitude and phase information of the time waveform of the sensor signal, for example. The extracting unit 130 may supply the extracted feature quantity to the comparing unit 150.

The storage unit 140 stores a walking model which represents walking motions based on feature quantities extracted from sensor signals corresponding to a predetermined number of steps of walking. The storage unit 140 stores the walking model acquired in advance. The walking model may be information about distribution of feature quantities extracted from output signals of a sensor carried by a collector of data for model creation when the collector walked a predetermined number of steps. In addition, the storage unit 140 stores a non-walking model which represents non-walking motions based on feature quantities extracted from sensor signals corresponding to non-walking motions. The storage unit 140 may store the non-walking model acquired in advance. The non-walking model may be information about distribution of feature quantities extracted from output signals of a sensor carried by a collector of data for model creation when the collector made non-walking motions.

In addition, the storage unit 140 may store intermediate data, calculation results, parameters or the like generated (or utilized) by the pedometer device 100 in the course of operation. In addition, upon receiving a request from each unit in the pedometer device 100, the storage unit 140 may supply stored data to a requestor of the request. For example, upon receiving a request from the comparing unit 150, the storage unit 140 supplies stored information to the comparing unit 150.

The comparing unit 150 compares a feature quantity of a sensor signal based on an estimated period with a walking model. The comparing unit 150 may compare a feature quantity extracted at the extracting unit 130 with a walking model read out from the storage unit 140. In addition, the comparing unit 150 may compare a feature quantity of a sensor signal based on an estimated period with a non-walking model. The comparing unit 150 may read out a non-walking model from the storage unit 140. The comparing unit 150 supplies a result of the comparison to the deciding unit 160.

The deciding unit 160 decides whether the user walked a predetermined number of steps based on a result of the comparison performed by the comparing unit. The deciding unit 160 decides whether or not the user actually walked a predetermined number of steps in the estimated period, based on a result of the comparison performed by the comparing unit 150. The deciding unit 160 outputs a result of the decision as user's step count information.

As mentioned above, the pedometer device 100 according to the present embodiment divides an acquired sensor signal for each estimated period during which the user apparently has walked a predetermined number of steps, and executes pattern matching or the like for each divided period to thereby decide, for each period, whether or not the user really walked a predetermined number of steps. Operations of such a pedometer device 100 are explained next.

Figure 2:
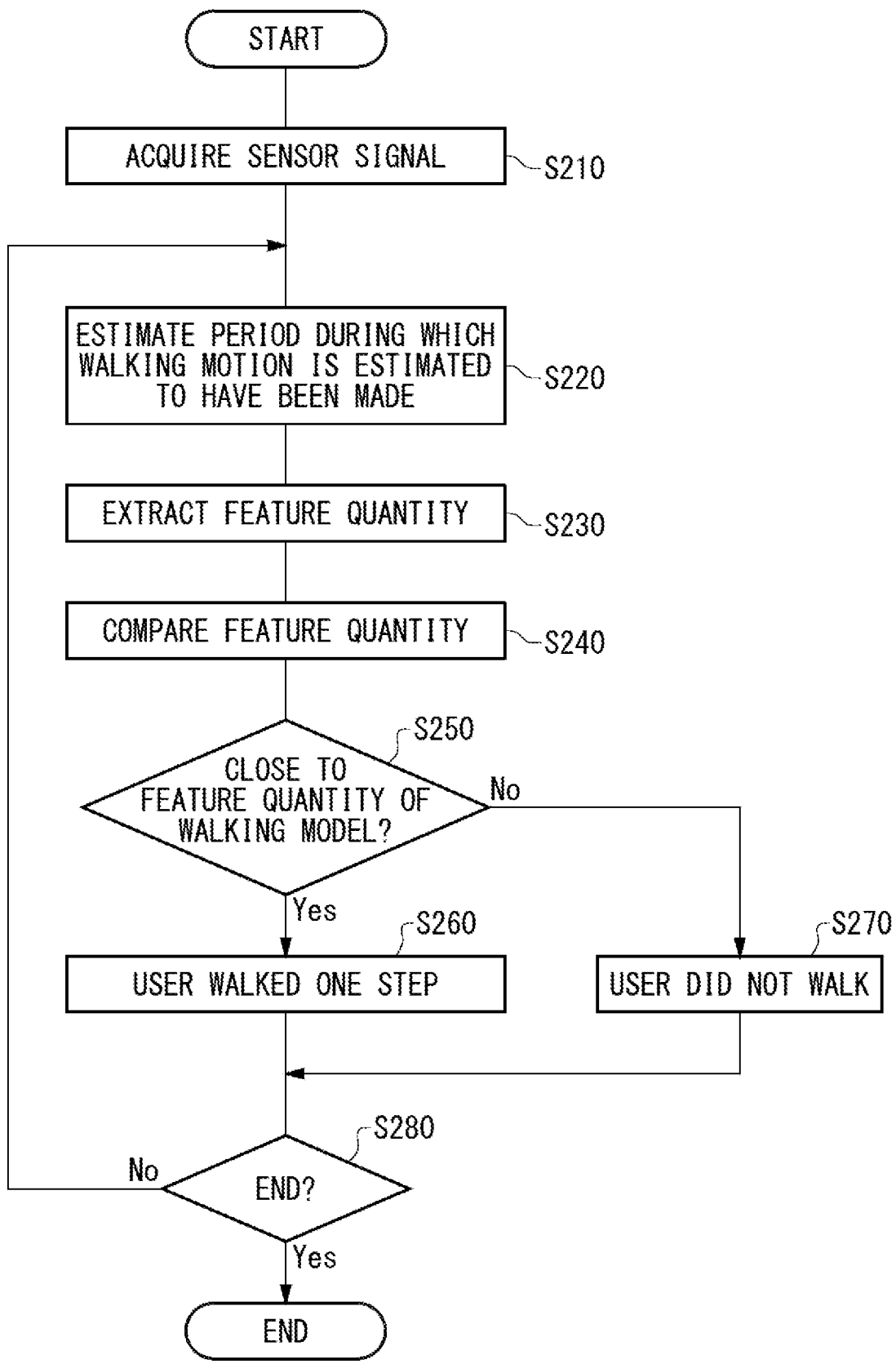
FIG. 2 illustrates an exemplary flow of operations performed by the pedometer device 100 according to the present embodiment.

FIG. 2 illustrates an exemplary flow of operations performed by the pedometer device 100 according to the present embodiment. The pedometer device 100 executes the operation flow illustrated in FIG. 2, and estimates and outputs user's step count information. Note that the pedometer device 100 may output user's step count information in real time.

First, the acquiring unit 110 acquires a sensor signal from the sensor 10 carried by the user (S210). The acquiring unit 110 may acquire sensor signals from multiple types of sensors 10. The acquiring unit 110 may acquire sensor signals in time periods each having a predetermined length or in units of a predetermined data amount. The acquiring unit 110 desirably acquires data corresponding to a period which is at least long enough the user to walk a few steps. In the present embodiment explained, the acquiring unit 110 acquires sensor signals from an acceleration sensor and an angular velocity sensor.

Next, based on the sensor signals, the estimating unit 120 estimates an estimated time period during which the user apparently has walked a predetermined number of steps (S220). In the present embodiment explained, the estimating unit 120 estimates an estimated period during which the user apparently has walked one step. The estimating unit 120 may detect oscillation of the user in the direction of gravity according to the time waveforms of the sensor signals, and estimate the period. When the user makes a walking motion, the speed and acceleration in the direction of gravity oscillate over time corresponding to the walking motion of the user. For example, if the user walks in one direction at an approximately constant speed, sensor signals associated with motions in the direction of gravity oscillate in an approximately constant cycle according to the walking speed of the user.

Figure 3:
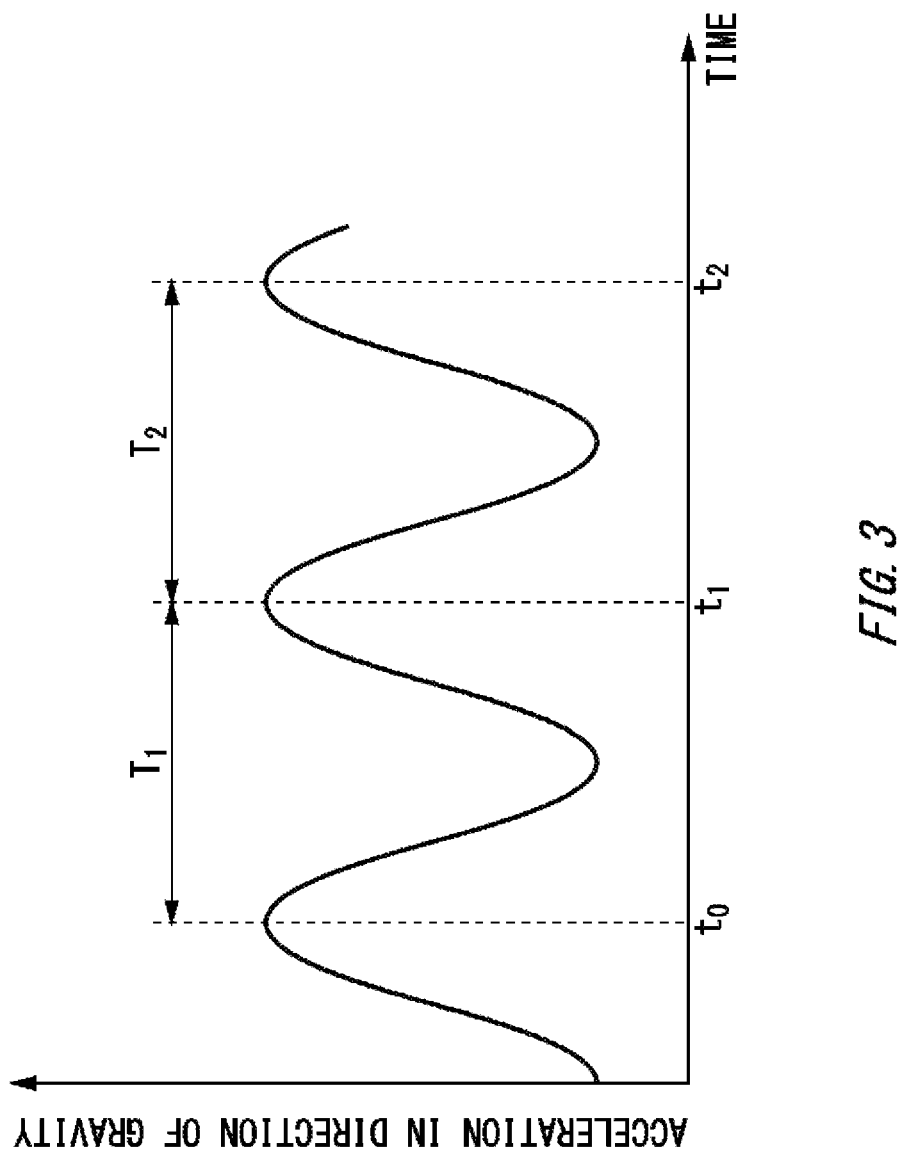
FIG. 3 illustrates an exemplary sensor signal acquired by an acquiring unit 110 according to the present embodiment.

FIG. 3 illustrates an exemplary sensor signal acquired by the acquiring unit 110 according to the present embodiment. FIG. 3 illustrates exemplary acceleration in the direction of gravity of the user who is walking, the acceleration being acquired by the acquiring unit 110 from the acceleration sensor carried by the user. In FIG. 3, the horizontal axis corresponds to time, and the vertical axis corresponds to acceleration in the direction of gravity. As illustrated in FIG. 3, the sensor signal oscillates between high and low signal strengths corresponding to the vertical oscillation resulting from the walking motion of the user. In addition, since the sensor signal in FIG. 3 appears to have a waveform that oscillates in an approximately constant cycle, it is estimated that the user is walking at an approximately constant speed.

In view of this, the estimating unit 120 may detect times at which approximately the same values are observed for the speed or acceleration of the user in the direction of gravity at local maximum values, local minimum values, medians, or the like, and estimate a period during which the user apparently has walked one step. For example, the estimating unit 120 detects two times at which a sensor signal of the acceleration sensor show two consecutive local maximum values, and estimates that the a period defined by those two times (time difference) as a period during which the user is estimated have moved forward by one step. FIG. 3 illustrates an example in which the estimating unit 120 detects, as $t_0$, $t_1$, $t_2$, times at which the sensor signal shows local maximum values, and sequentially estimates, as $T_1$, $T_2$, . . . , periods during which the user apparently has moved forward by one step. Note that if extreme values of a sensor signal are not detected, the estimating unit 120 may determine that the user is standing still, and may not estimate periods about the time region.

Next, the extracting unit 130 extracts a feature quantity of a sensor signal (S230). The extracting unit 130 may extract a feature quantity of each sensor signal for each estimated period. In addition, the extracting unit 130 may extract a feature quantity of a sensor signal in a predetermined direction relative to the user's advancing direction. For example, the extracting unit 130 extracts feature quantities of a sensor signal of the acceleration sensor in the advancing direction, and a sensor signal of the angular velocity sensor in the horizontal direction relative to the advancing direction. The extracting unit 130 may extract, as feature quantities, the amplitude strength, phase information, and the like of sensor signals.

Figure 4:
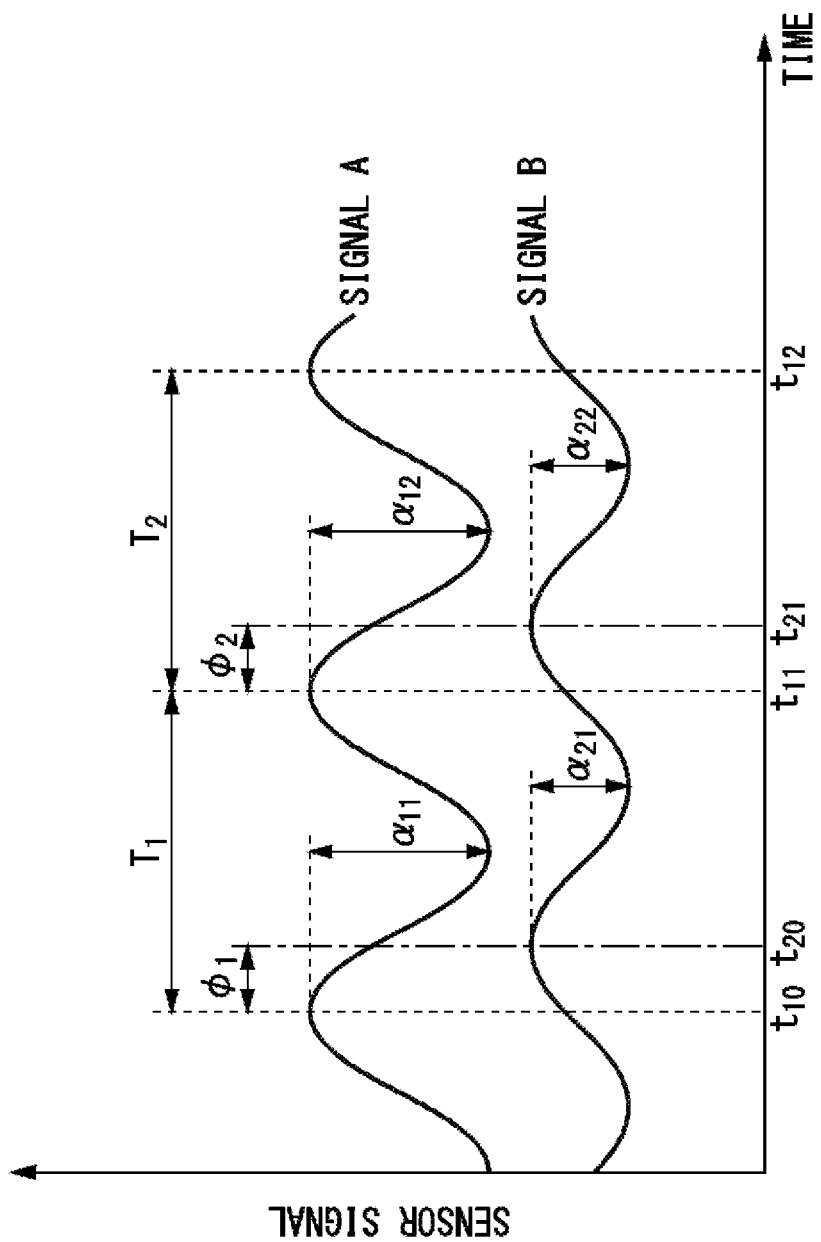
FIG. 4 illustrates an exemplary feature quantity of a sensor signal extracted by an extracting unit 130 according to the present embodiment.

FIG. 4 illustrates an exemplary feature quantity of a sensor signal extracted by the extracting unit 130 according to the present embodiment. FIG. 4 illustrates exemplary acceleration in the direction of gravity, and exemplary acceleration in the advancing direction of the user who is walking, the acceleration being acquired by the acquiring unit 110 from the acceleration sensor carried by the user. In FIG. 4, the horizontal axis corresponds to time, and the vertical axis corresponds to relative strength of sensor signals (that is, acceleration). In FIG. 4, the acceleration in the direction of gravity is illustrated by the signal A, and the acceleration in the advancing direction is illustrated by the signal B. The signal A and signal B oscillate between high and low signal strengths corresponding to up and down motions and forward and backward motions resulting from a walking motion of the user.

As illustrated in FIG. 4, if the estimating unit 120 estimated the periods $T_1$, $T_2$, . . . using the signal A, the extracting unit 130 extracts feature quantities of the signal A and signal B. Note that the periods $T_1$, $T_2$, . . . indicate time differences $t_{11}-t_{10}$, $t_{12}-t_{11}$, . . . between times $t_1$, $t_{11}$, $t_{12}$, . . . at which the signal A shows local maximum values. In the period $T_1$ of the signal A, the extracting unit 130 may extract, as feature quantities, the amplitude value $\alpha_{11}$ which is the difference between a local maximum value and a local minimum value, and the period $T_1=t_{11}-t_{10}$. In addition, in the period $T_2$ of the signal A, the extracting unit 130 may extract, as feature quantities, the amplitude value $\alpha_{12}$, and the period $T_2=t_{12}-t_{11}$.

In the period $T_1$ of the signal B, the extracting unit 130 may extract the amplitude value $\alpha_{21}$ as a feature quantity. In addition, the extracting unit 130 may extract, as a feature quantity, information about the phase difference from the signal A as a feature quantity of the signal B. For example, if the estimating unit 120 estimates the period $T_1$ of the signal A as the time difference $t_{11}-t_{10}$ between local maximum values that are next to each other, the extracting unit 130 extracts, as the phase difference $\varphi_1$, the time difference between the start time $t_{10}$ of the period $T_1$ and the time $t_{20}$ which is in the period $T_1$ and at which a local maximum value value of the signal B is observed. In addition, in the period $T_2$ of the signal B, the extracting unit 130 may extract, as feature quantities, the amplitude value $\alpha_{22}$, and the phase difference $\varphi_2=t_{21}-t_{11}$.

In addition, if the acquiring unit 110 acquires a sensor signal of another sensor, the extracting unit 130 may similarly extract a feature quantity of each period. For example, if the acquiring unit 110 acquires a sensor signal of an angular velocity in the approximately horizontal direction relative to the user's advancing direction, the extracting unit 130 extracts a feature quantity from the time waveform of the angular velocity. For example, the extracting unit 130 may extract, as feature quantities, the amplitude of the angular velocity (the difference between a local maximum value and a local minimum value), and the phase difference (the difference between the start time of a period and a time at which a local maximum value is detected).

Next, the comparing unit 150 compares a feature quantity of a sensor signal based on an estimated period with a walking model (S240). The comparing unit 150 may compare a feature quantity of each period of a sensor signal extracted by the extracting unit 130 with a walking model stored in advance on the storage unit 140. In addition, the comparing unit 150 may compare a feature quantity of a sensor signal based on an estimated period with a non-walking model. The comparing unit 150 may compare a feature quantity of each period of a sensor signal extracted by the extracting unit 130 with a non-walking model stored in advance on the storage unit 140.

Here, the storage unit 140 may calculate, through simulation or the like, feature quantities that should be extracted when a predetermined number of steps of walking motion and a non-walking motion are executed, and store information about distribution of them. In addition, if a predetermined number of steps of walking motion and a non-walking motion are executed, the storage unit 140 may store information about distribution of feature quantities extracted from actually detected sensor signals.

The comparing unit 150 may compare corresponding feature quantities for each period. The comparing unit 150 may generate, and compare feature vectors having a plurality of feature quantities as components. That is, the comparing unit 150 may compare a feature vector having a feature quantity extracted by the extracting unit 130 as a component with a feature vector distribution indicated by a walking motion model or non-walking motion model stored on the storage unit. In this case, the comparing unit may output, as a comparison result, the similarity with the walking model or non-walking model.

Figure 5:
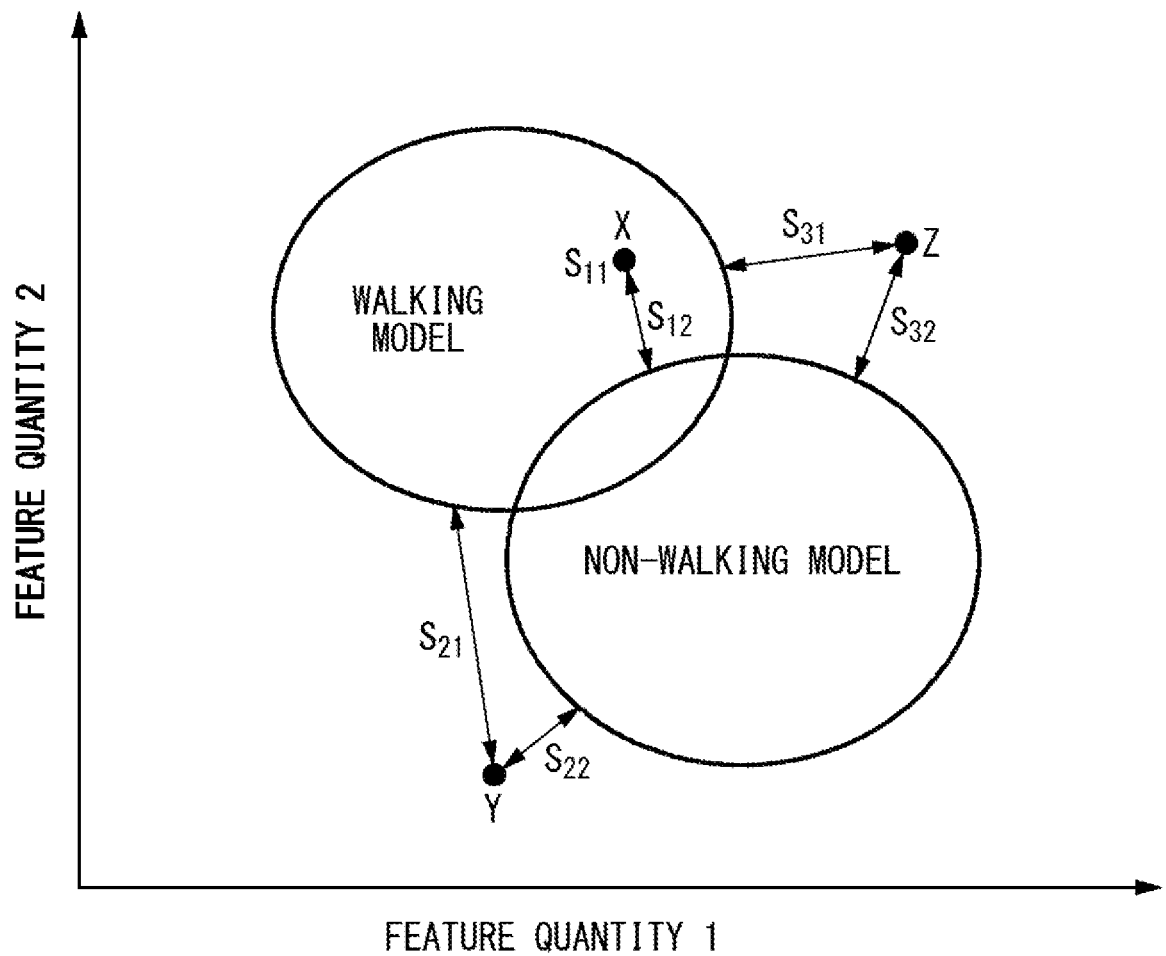
FIG. 5 illustrates an example schematically illustrating comparison performed by a comparing unit 150 according to the present embodiment.

FIG. 5 illustrates an example schematically illustrating comparison performed by the comparing unit 150 according to the present embodiment. In FIG. 5, the horizontal axis corresponds to a feature quantity 1, and the vertical axis corresponds to a feature quantity 2. The number of feature quantities extracted by the extracting unit 130 is desirably three or more, but it is difficult to simply illustrate an n-dimensional space, and so FIG. 5 illustrates an example in which a feature quantity space is simply expressed as a two-dimensional plane. In this case, for example, a feature vector is expressed as (feature quantity 1, feature quantity 2).

The distribution of feature quantities constituting a walking model stored on the storage unit 140 has a finite extent depending on walking speeds, motions executed along with walking motions, presence or absence of baggage, and the like. The distribution of feature quantities constituting a non-walking model similarly has a finite extent depending on types of motion, and the like. FIG. 5 illustrates examples of the distribution of feature quantities constituting such a walking model, and the distribution of feature quantities constituting such a non-walking model. FIG. 5 illustrates ranges of the respective models where their constituent feature quantities are densely located, that is, ranges corresponding to high likelihood. The comparing unit 150 compares the distributions of feature quantities with an extracted feature quantity. For example, if a point X (feature quantity $1_N$, feature quantity $2_N$) determined by a feature quantity $1_N$, and a feature quantity $2_N$ extracted by the extracting unit 130 in a period $T_N$ is in the range where feature quantities constituting the walking model are densely located, the comparing unit 150 may output a comparison result that the similarity $S_{11}$ with the walking model is high (for example, 8).

In addition, the comparing unit 150 may calculate the similarity between the point X and the non-walking model, and output the similarity as the comparison result (for example, 3). Note that the similarity with each model may be the reciprocal $S_{12}$ of the shortest distance among the distances to feature quantities constituting the model. In addition, the similarity with each model may be a value calculated based on the distribution function of feature quantities constituting the model. In addition, the similarity may be relative values. In addition, the extracting unit 130 may weight feature quantities so as to increase or decrease the influence of a particular feature quantity. In this case, the storage unit 140 also may store weighted feature quantities.

The comparing unit 150 may execute such comparison sequentially for each period. For example, if a feature quantity of a next period $T_{N+1}$ extracted next by the extracting unit 130 is at the point Y (feature quantity $1_{N+1}$, feature quantity $2_{N+1}$), the comparing unit 150 outputs the similarity $S_{21}$ (for example, 1) of the point Y with the walking model, and the similarity $S_{22}$ of the point Y with the non-walking model (for example, 4) as a comparison result. In addition, if a feature quantity of a next period $T_{N+2}$ extracted further by the extracting unit 130 is at the point Z (feature quantity $1_{N+2}$, feature quantity $2_{N+2}$), the comparing unit 150 outputs the similarity $S_{31}$ (for example, 2) of the point Z with the walking model, and the distance $S_{32}$ (for example, 3) of the point Z from the non-walking model as a comparison result.

Next, the deciding unit 160 decides a motion of the user based on a result of the comparison performed by the comparing unit 150 (S250 to S270). If a feature quantity extracted by the extracting unit 130 has a high similarity with the walking model, the deciding unit 160 decides that the user is walking (S250: Yes). For example, if a similarity with the walking model, which is a comparison result, is higher than a predetermined threshold (for example, 5), the deciding unit 160 decides that the user is walking. In the example illustrated in FIG. 5, since the point X has a similarity with the walking model which is 8, the user is decided as making a walking motion in the period $T_N$. Then, since the period is an estimate value of a period during which the user apparently has walked one step, the deciding unit 160 may decide the user's step count in the period $T_N$ as 1 (S260).

In addition, if a feature quantity extracted by the extracting unit 130 has a high similarity with the non-walking model, the deciding unit 160 decides that the user is not walking (S250: No). For example, if a similarity with the non-walking model, which is a comparison result, is higher than a predetermined threshold (for example, 3.5), the deciding unit 160 decides that the user is not walking. In the example illustrated in FIG. 5, since the point Y has a similarity with the non-walking model which is 4, the user is decided as making a non-walking motion in the period $T_{N+1}$. The deciding unit 160 may decide the user's step count in the period $T_{N+1}$ as 0 (S270).

In addition, if a feature quantity extracted by the extracting unit 130 has low similarities with the walking model and non-walking model, the deciding unit 160 may decide that the user is not walking (S250: No). For example, if similarities with the walking model and non-walking model, which are comparison results, are lower than predetermined thresholds, the deciding unit 160 decides that the user is not walking. In the example illustrated in FIG. 5, since the point Z has a similarity with the walking model which is 2, and a similarity with the non-walking model which is 3, and both the values are lower than the thresholds, the user is decided as making a non-walking motion in the period $T_{N+2}$. The deciding unit 160 may decide the user's step count in the period $T_{N+2}$ as 0 (S270).

If the pedometer device 100 continues counting the number of user's steps (S280: No), the pedometer device 100 returns to an estimation of a period by the estimating unit 120 (S220). That is, the pedometer device 100 estimates the next period, extracts a feature quantity in the estimated period, compares the feature quantity with each of the walking model and the non-walking model, and decides the user's step count.

Instead of this, if the estimating unit 120 first executes estimations of all the periods of sensor signals, the pedometer device 100 may return to extraction of feature quantities by the extracting unit 130 (S230). In addition, furthermore, if the extracting unit 130 first executes extraction of feature quantities for all the periods, the pedometer device 100 may return to comparison by the comparing unit 150 (S240). In addition, if the pedometer device 100 completes decision of the numbers of user's steps about all the sensor signals that are acquired by the acquiring unit 110 temporally sequentially, the pedometer device 100 may return to acquisition of a sensor signal (S210), and further continue decision about the user's step count. In this manner, the pedometer device 100 may sequentially decide the user's step count for each period.

In addition, upon receiving an instruction or the like from the outside, the pedometer device 100 may suspend or stop decision about the user's step count (S280: Yes). Upon receiving, from the user, an input instructing to stop operation, or an instruction instructing suspension or stop from a system connected externally or the like, the pedometer device 100 may suspend or stop operation.

As mentioned above, the pedometer device 100 according to the present embodiment estimates, as a period during which the user apparently has walked a predetermined number of steps, a period during which vertical oscillation of the user is detected, and compares a feature quantity extracted in the period with a model to thereby decide whether or not the user really walked a predetermined number of steps. Accordingly, even if vertical oscillation of the user is detected because of stamp, lowering/raising of baggage, knee flexion, or the like despite the user is not walking, the pedometer device 100 allows reduction of false counts of the user's step counts by comparing an extracted feature quantity with each of a non-walking motion model which represents non-walking motions like those mentioned above, and a walking motion model.

Note that although the user might continue a walking motion, the user might stop walking after each step if he/she is answering a phone, manipulating a mobile terminal or the like, and so on. In addition, the user might walk at different speeds, change the advancing direction, walk while changing the advancing direction, or stamp. By setting a shorter period for a period, based on which the user is estimated as making a walking motion, that is, for example by treating each step as corresponding to a single period, the pedometer device 100 can cope with various motions of the user like those mentioned above, and count the number of user's steps precisely.

Note that the pedometer device 100 according to the present embodiment is explained as acquiring a sensor signal from a sensor worn at a trunk portion such as the waist of the user. Instead of this, the sensor may be worn at an arm or the like of the user. Here, an arm of the user relatively moves forward and backward along with walking, and relatively returns to its initial position after the user walks two steps. That is, the sensor worn at the arm detects vertical oscillation along with such swings of the arm of the user.

In order to extract such swings of the arm as a feature quantity, and separate it from a walking motion, the pedometer device 100 desirably estimates, as one period, a period corresponding to a motion that is made until the swinging motion of the arm is completed. That is, in this case, the estimating unit 120 may estimate, as one period, a period during which the user's step count reached two. In this case, if the deciding unit 160 decides that the user is walking based on one period, the deciding unit 160 may decide the user's step count of the one period as two.

In the pedometer device 100 according to the above-mentioned present embodiment explained, the acquiring unit 110 acquires sensor signals about acceleration in the user's advancing direction, and an angular velocity in the approximately horizontal direction relative to the advancing direction. That is, the pedometer device 100 uses sensor signals in the case where the user's advancing direction is known to count the user's step count. In addition to this, the pedometer device 100 may further estimate the user's advancing direction. Note that the advancing direction means the advancing direction in a sensor coordinate system.

In this case also, a walking model stored on the storage unit 140 is based on feature quantities extracted from sensor signals under the condition that the advancing direction and approximately horizontal direction are known.

Figure 6:
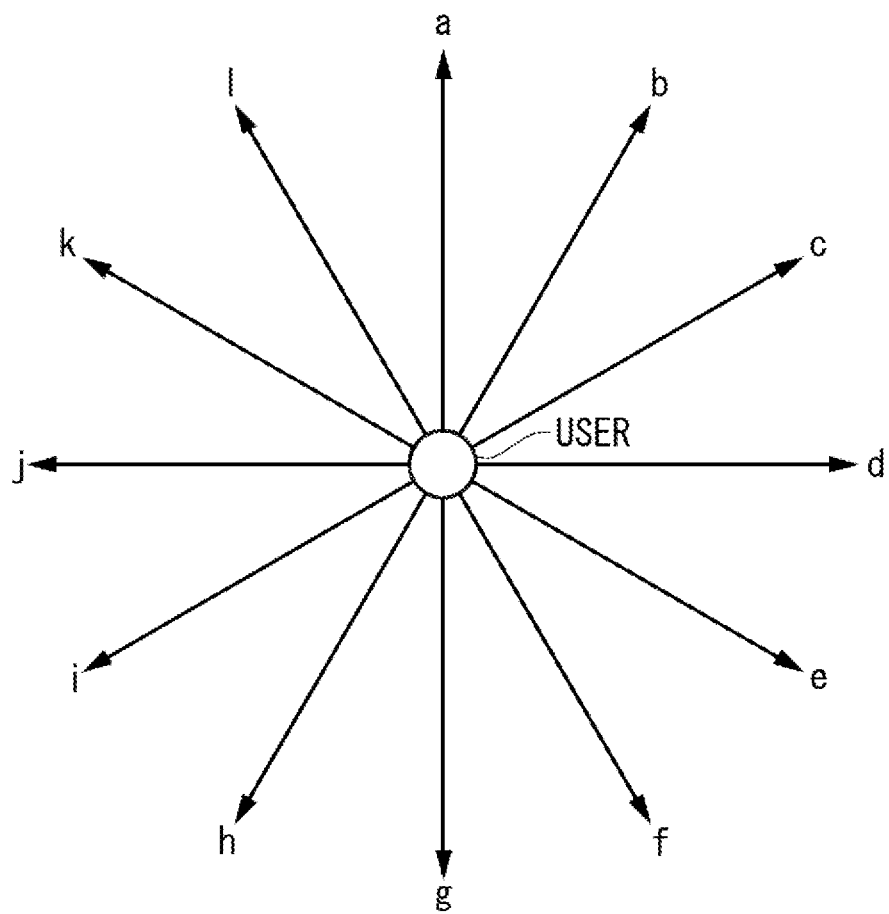
FIG. 6 illustrates exemplary candidates of a user's advancing direction estimated by the pedometer device 100 according to the present embodiment.

FIG. 6 illustrates exemplary candidates of a user's advancing direction estimated by the pedometer device 100 according to the present embodiment. FIG. 6 illustrates an exemplary horizontal plane on which the user is located. FIG. 6 illustrates an example in which the pedometer device 100 divides candidates of the advancing direction into twelve directions including the direction a to the direction 1 with the user at the center of the directions. The pedometer device 100 extracts, from a sensor signal, a feature quantity assuming that each candidate is the advancing direction. That is, the extracting unit 130 extracts feature quantities of sensor signals about candidates of the user's advancing direction.

Then, the comparing unit 150 compares feature quantities extracted about the candidates of the advancing direction by the extracting unit 130 with the walking model stored on the storage unit 140. A similarity is calculated for each advancing direction candidate, and output as a comparison result.

FIG. 7 illustrates an exemplary comparison result output by the comparing unit 150 according to the present embodiment. For each direction among the advancing direction a to the advancing direction 1 which are the advancing direction candidates, the comparing unit 150 calculates and outputs the similarity $S_{a1}$ to $S_{11}$ of an extracted feature quantity with a walking model, and the similarity $S_{a2}$ to $S_{12}$ of the extracted feature quantity with a non-walking model. The deciding unit 160 further decides the advancing direction based on such comparison results. The deciding unit 160 may decide an advancing direction candidate with the highest similarity with the walking model as the user's advancing direction.

Figure 8:
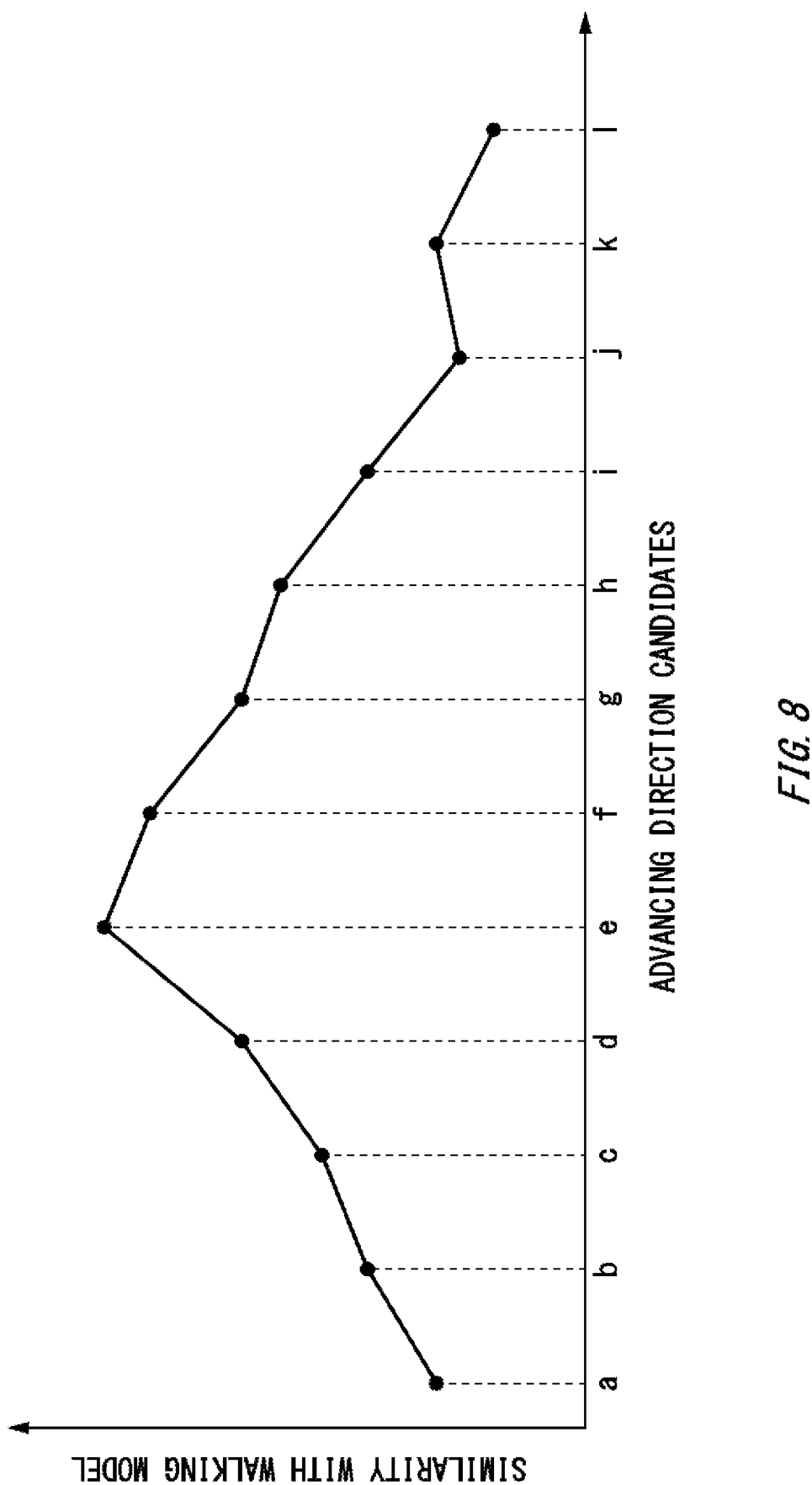
FIG. 8 illustrates an exemplary process of deciding a user's advancing direction by a deciding unit 160 according to the present embodiment.

FIG. 8 illustrates an exemplary process of deciding a user's advancing direction by a deciding unit 160 according to the present embodiment. In FIG. 8, the horizontal axis corresponds to user's advancing direction candidates, and the vertical axis corresponds to results of comparison performed by the comparing unit 150. The deciding unit 160 decides, as the advancing direction, a direction that gives a feature quantity which is observed in a period during which vertical oscillation of the user is detected, and has the highest similarity with the walking model. In the example illustrated in FIG. 8, the deciding unit 160 may decide the direction e as the user's advancing direction.

If the deciding unit 160 decides the user's advancing direction, the deciding unit 160 decides the user's step count using a result of comparison performed by the comparing unit 150 corresponding to the direction. For example, if the deciding unit 160 decides the direction e as the user's advancing direction, the deciding unit 160 decides whether or not the user is making a walking motion using the similarity $S_{e1}$ with the walking model, and the similarity $S_{e2}$ with the non-walking model. That is, the deciding unit 160 decides a motion of the user according to a result of comparison of the distance $S_{e1}$ and distance $S_{e2}$ with predetermined thresholds. The deciding unit 160 may further decide the user's step count. That is, if the deciding unit 160 decides the user's step count based on a result of comparison performed by the comparing unit 150, the deciding unit 160 can decide the step count along with the user's advancing direction.

As mentioned above, the pedometer device 100 according to the present embodiment can estimate the user's advancing direction and step count based on sensor signals acquired from the sensor 10. In addition, since the pedometer device 100 estimates also the user's advancing direction for each cycle of vertical oscillation of the user, the pedometer device 100 can estimate changes in the advancing direction precisely even if the user is walking while changing the advancing direction after each step, for example. In addition, since the pedometer device 100 can estimate changes in the user's advancing direction precisely, the pedometer device 100 can estimate the user's step count based on the advancing direction precisely.

Various embodiments of the present invention may be described with reference to flowcharts and block diagrams whose blocks may represent (1) steps of processes in which operations are performed or (2) sections of apparatuses responsible for performing operations. Certain steps and units may be implemented by dedicated circuitry, programmable circuitry supplied with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), etc.

Computer-readable media may include any tangible device that can store instructions for execution by a suitable device, such that the computer-readable medium having instructions stored therein comprises an article of manufacture including instructions which can be executed to create means for performing operations specified in the flowcharts or block diagrams. Examples of computer-readable media may include an electronic storage medium, a magnetic storage medium, an optical storage medium, an electromagnetic storage medium, a semiconductor storage medium, etc. More specific examples of computer-readable media may include a floppy disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a BLU-RAY (registered trademark) disc, a memory stick, an integrated circuit card, etc.

Computer-readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, JAVA (registered trademark), C++, etc., and conventional procedural programming languages, such as the "C" programming language or similar programming languages.

Computer-readable instructions may be provided to a processor of a general purpose computer, special purpose computer, or other programmable data processing apparatus, or to programmable circuitry, locally or via a local area network (LAN), wide area network (WAN) such as the Internet, etc., to execute the computer-readable instructions to create means for performing operations specified in the flowcharts or block diagrams. Examples of processors include computer processors, processing units, microprocessors, digital signal processors, controllers, microcontrollers, etc.

Figure 9:
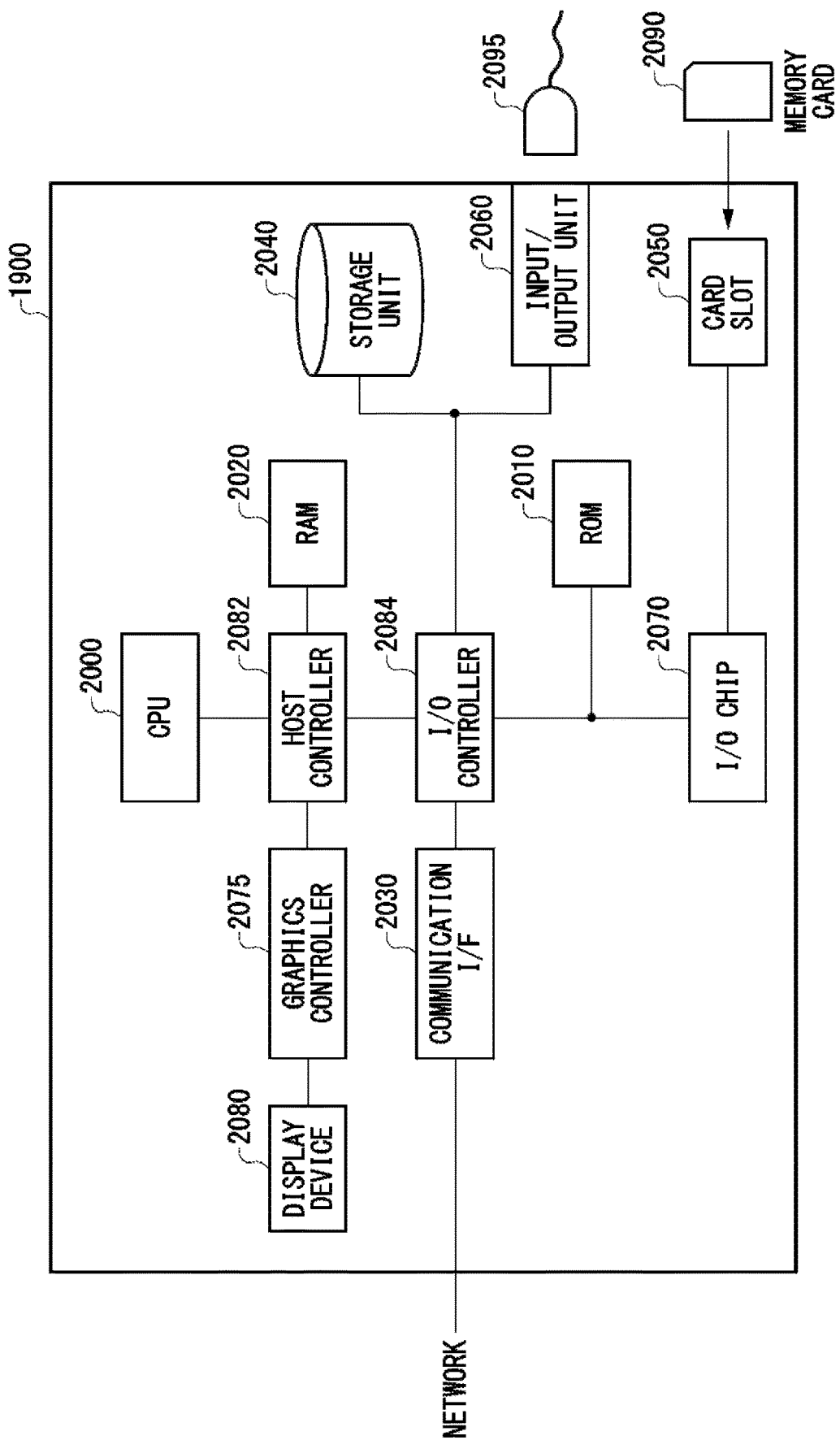
FIG. 9 illustrates an exemplary hardware configuration of a computer 1900 to function as the pedometer device 100 according to the present embodiment.

FIG. 9 illustrates an exemplary hardware configuration of a computer 1900 to function as the pedometer device 100 according to the present embodiment. The computer 1900 according to the present embodiment is mounted inside the housing along with the sensor 10, for example. Instead of this, the computer 1900 is provided outside the housing in which the sensors are housed, and may receive sensor output from the sensor 10.

The computer 1900 comprises: a CPU peripheral unit having a CPU 2000, a RAM 2020, a graphics controller 2075 and a display device 2080 that are interconnected by a host controller 2082; a communication interface 2030, a storage unit 2040 and an input/output unit 2060 that are connected to the host controller 2082 by an input/output controller 2084; a ROM 2010; a card slot 2050; and an input/output chip 2070.

The host controller 2082 connects the RAM 2020, and the CPU 2000 and graphics controller 2075 that access the RAM 2020 at high transfer rates. The CPU 2000 operates based on a program stored on the ROM 2010 and the RAM 2020, and controls each unit. The graphics controller 2075 acquires image data to be generated on a frame buffer provided within the RAM 2020 by the CPU 2000 or the like, and displays the image data on the display device 2080. Instead of this, the graphics controller 2075 may include therein a frame buffer that stores image data generated by the CPU 2000 or the like.

The input/output controller 2084 connects the host controller 2082, and the communication interface 2030, storage unit 2040 and input/output unit 2060 that are relatively high speed input/output devices. The communication interface 2030 communicates with other devices via a network. The storage unit 2040 stores therein a program and data to be used by the CPU 2000 within the computer 1900. The storage unit 2040 is a non-volatile memory, and for example is a flash memory, hard disk, or the like.

The input/output unit 2060 is connected with a connector 2095, transmits and receives a program or data to and from the outside, and provides them to the storage unit 2040 via the RAM 2020. The input/output unit 2060 may transmit and receive the program and data to and from the outside by standardized connectors and communication methods, and in this case the input/output unit 2060 may use standards such as USB, IEEE1394, HDMI (registered trademark), or Thunderbolt (registered trademark). In addition, the input/output unit 2060 may transmit and receive the program and data to and from the outside using wireless communication standards such as Bluetooth (registered trademark).

In addition, the ROM 2010, and relatively low speed input/output devices of the card slot 2050 and input/output chip 2070 are connected to the input/output controller 2084. The ROM 2010 stores therein a boot-program that the computer 1900 executes at the time of start-up and/or a program that is dependent on hardware of the computer 1900, or the like. The card slot 2050 reads out a program or data from the memory card 2090, and provides them to the storage unit 2040 via the RAM 2020. The input/output chip 2070 may connect the card slot 2050 to the input/output controller 2084, and also connect various types of input/output devices to the input/output controller 2084 via, for example, a parallel port, a serial port, a keyboard port, a mouse port or the like.

A program to be provided to the storage unit 2040 via the RAM 2020 is provided by a user via the input/output unit 2060 or by being stored on a recording medium such as the memory card 2090. The program is read out from the recording medium, installed in the storage unit 2040 within the computer 1900 via the RAM 2020, and executed in the CPU 2000.

The program is installed in the computer 1900, and causes the computer 1900 to function as the acquiring unit 110, estimating unit 120, extracting unit 130, storage unit 140, comparing unit 150, and deciding unit 160.

Information processing described in the program is read by the computer 1900 to function as the acquiring unit 110, estimating unit 120, extracting unit 130, storage unit 140, comparing unit 150, and deciding unit 160 which are specific means that are realized by cooperation between software and the various types of hardware resources described above. Then, by realizing, with these specific means, operations or processing on information according to purposes of usage of the computer 1900 in the present embodiment, the unique pedometer device 100 according to the purposes of usage is constructed.

For example, when communication is performed between the computer 1900 and an external device or the like, the CPU 2000 executes a communication program loaded onto the RAM 2020, and based on the processing contents described in the communication program, instructs the communication interface 2030 to perform a communication process. Under control of the CPU 2000, the communication interface 2030 reads out transmitted data stored on a transmission buffer region or the like provided in the RAM 2020, the storage unit 2040, the memory card 2090, a storage connected via the input/output unit 2060, or the like like to transmit the data to a network, or writes received data received from a network into a reception buffer region or the like provided on a storage. In this manner, the communication interface 2030 may transfer transmitted/received data between storages by the DMA (direct memory access) scheme, or instead of this, the CPU 2000 may transfer transmitted/received data by reading out data from a transfer source storage or communication interface 2030, and writing the data into a transfer destination communication interface 2030 or storage.

In addition, the CPU 2000 causes all or necessary portions of files, databases or the like stored on the storage unit 2040, the memory card 2090, a storage connected via the input/output unit 2060, or the like to be read into the RAM 2020 by the DMA transfer or other schemes, and performs various types of processing on the data on the RAM 2020. Then, the CPU 2000 writes the data on which processing has been performed back into an external storage by the DMA transfer or other schemes. Because in such processing, the RAM 2020 can be regarded as holding contents of the external storage temporarily, the RAM 2020 and the external storage or the like are collectively called a memory, a storage unit, a storage or the like in the present embodiment. Various types of information such as various types of programs, data, tables, databases or the like in the present embodiment are stored on such a storage, and are subjected to information processing. Note that the CPU 2000 can also hold a portion of the RAM 2020 on a cache memory, and read out from and write in the cache memory. Because in such an embodiment also, the cache memory plays a role of some of functions of the RAM 2020, in the present embodiment, the cache memory is also regarded as being included in the RAM 2020, a memory and/or a storage unless otherwise they are distinguished from each other.

In addition, the CPU 2000 performs, on data read out from the RAM 2020, various types of processing including various types of operation, information processing, conditional judgment, information search/replacement or the like described in the present embodiment that are specified in an instruction sequence of a program, and writes the data back into the RAM 2020. For example, when performing conditional judgment, the CPU 2000 compares various types of variables illustrated in the present embodiment to judge whether they meet conditions such as being larger than, smaller than, equal to or larger than, equal to or smaller than other variables or constants, and when a condition is met (or when it is not met) branches to a different instruction sequence or calls up a subroutine.

In addition, the CPU 2000 can search information stored in files, databases or the like in a storage. For example, when a plurality of entries in which attribute values of a second attribute are respectively associated with attribute values of a first attribute are stored on a storage, the CPU 2000 searches, from among the plurality of entries stored on the storage, an entry whose attribute value of the first attribute matches a specified condition, and reads out the attribute value of the second attribute stored in the entry, thereby obtaining the attribute value of the second attribute associated with the first attribute that meets a predetermined condition.

The programs or modules illustrated above may be stored on an external recording medium. The recording medium to be used may be, other than the memory card 2090, an optical recording medium such as DVD, Blue-ray (registered trademark) or CD, a magneto-optical recording medium such as MO, a tape medium, a semiconductor memory such as IC card or the like. In addition, a storage such as a hard disk or a RAM provided to a server system connected to a dedicated communication network or the Internet may be used as a recording medium, and a program may be provided to the computer 1900 via the network.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method illustrated in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A pedometer device in conjunction with a sensor being worn by a user, the device comprising:
   an acquiring unit that acquires a sensor signal output by the sensor carried by a user;
   an estimating unit that estimates a time period during which the user apparently has made a walking motion by detecting when substantially the same values are observed for the sensor signal, the time period being an estimated period during which the user apparently has walked a predetermined number of steps;
   an extracting unit that extracts a feature quantity occurring in the estimated time period from the sensor signal;
   a storage unit that stores a walking model which represents walking motions and a non-walking model which represents non-walking motions, the walking model being formed based on a feature quantity extracted from a sensor signal corresponding to a predetermined number of steps of walking, and the non-walking model being formed based on a feature quantity extracted from a sensor signal corresponding to a non-walking motion:
   a comparing unit that compares the feature quantity extracted at the extracting unit with the walking model and compares the feature quantity extracted at the extracting unit with the non-walking model: and
   a deciding unit that decides whether the user has walked a predetermined number of steps, based on a result of the comparison performed by the comparing unit.

2. The pedometer device according to claim 1, wherein the extracting unit extracts a feature quantity of the sensor signal for at least one candidate of an advancing direction of the user, the comparing unit compares, with the walking model, the feature quantity extracted for at least one candidate of the advancing direction, and the deciding unit further decides the advancing direction based on a result of the comparison performed by the comparing unit.

3. The pedometer device according to claim 1, wherein the sensor includes an acceleration sensor.

4. The pedometer device according to claim 1, wherein the sensor includes an angular velocity sensor.

5. The pedometer device according to claim 1, further comprises a housing wherein the sensor and the pedometer device are located within the housing.

6. A step counting method in conjunction with a sensor being worn by a user, the method comprising:
   acquiring a sensor signal output by the sensor carried by a user; estimating a time period during which the user apparently has made a walking motion by detecting when substantially the same values are observed for the sensor signal, the time period being an estimated period during which the user apparently has walked a predetermined number of steps;
   extracting a feature quantity occurring in the estimated time period from the sensor signal;
   comparing the feature quantity extracted in the extracting with a walking model and a non-walking model, the walking model representing walking motions and being formed based on a feature quantity extracted from a sensor signal corresponding to a predetermined number of steps of walking, and the non-walking model representing non-walking motions and being formed based on a feature quantity extracted from a sensor signal corresponding to a non-walking motion; and
   deciding whether the user has walked a predetermined number of steps, based on a result of the comparison.

* * * * *